(12) United States Patent
Oliver et al.

(10) Patent No.: US 6,297,513 B1
(45) Date of Patent: Oct. 2, 2001

(54) EXPOSURE SERVO FOR OPTICAL NAVIGATION OVER MICRO-TEXTURED SURFACES

(75) Inventors: Thomas C Oliver, Windsor; Brian L. Hastings, Fort Collins, both of CO (US)

(73) Assignee: Hewlett-Packard Company, Palo Alto, CA (US)

(*) Notice: Subject to any disclaimer, the term of this patent is extended or adjusted under 35 U.S.C. 154(b) by 0 days.

(21) Appl. No.: 09/428,928

(22) Filed: Oct. 28, 1999

(51) Int. Cl.$^7$ .................................................. G01N 21/86
(52) U.S. Cl. ........................................ 250/548; 250/559.3
(58) Field of Search ............................. 250/548, 559.29, 250/559.3, 208.1, 557; 356/399–401; 235/462.2, 462.23

(56) References Cited

U.S. PATENT DOCUMENTS 5,051,770 * 9/1991 Cornuejols ........................... 396/166

* cited by examiner

Primary Examiner—Que T. Le

(57) ABSTRACT

Independent of any of several ways used to control exposure for the optical sensor in an optical navigation device, changes in average level of illumination are taken as indicative of changes in exposure. An acceptable exposure level for an optical navigation system is maintained by first establishing an initial operating level of exposure and subsequently adjusting it in proportion to changes in average illumination so long as image contrast remains acceptable. Associated with the initial operating level of exposure is an average level of illumination, which is then noted, and about which is presumed to exist a range of satisfactory operating levels for exposure. The system proceeds to navigate from the current reference frame using this level of exposure. When a new reference frame is established the average level of illumination and the image contrast are checked. If the illumination is within the range of presumed satisfactory operating levels for exposure and the image contrast is within acceptable limits, then no change is made to the parameter that adjusts exposure and navigation proceeds from the new reference frame. If average level of illumination is outside the presumed satisfactory range, but the image contrast is still acceptable, a proportional correction is made to the parameter controlling exposure, and navigation proceeds. In all other cases the contrast is unacceptable, and the remedies are to variously re-enter the process that establishes an initial operating level for exposure.

6 Claims, 3 Drawing Sheets

EXPOSURE SERVO FOR OPTICAL NAVIGATION OVER MICRO-TEXTURED SURFACES

INCORPORATIONS BY REFERENCE

The subject matter of the present application is related to that disclosed in U.S. Pat. No. 5, 644, 139, entitled NAVIGATION TECHNIQUE FOR DETECTING MOVEMENT OF NAVIGATION SENSORS RELATIVE TO AN OBJECT (issued Jul. 1 1997), to that disclosed in U.S. Pat. 5, 729, 008, entitled METHOD AND DEVICE FOR TRACKING RELATIVE MOVEMENT BY CORRELATING SIGNALS FROM AN ARRAY OF PHOTO ELEMENTS (issued Mar. 17 1998), and also to that disclosed in U.S. patent application 09/052, 046 entitled "SEEING EYE" MOUSE FOR A COMPUTER SYSTEM (filed Ma. 30 1998). In the interest of brevity, U.S. Pat. Nos. 5, 644, 139 & 5,729,008 and U.S. application Ser. No. 09/052, 046 are each hereby incorporated herein by reference.

BACKGROUND OF THE INVENTION

A recently developed technique of tracking motion and accumulating position by correlating shifted instances of a previous image with new images of surface micro-texture, such as the fibers in a sheet of paper, offers ease of use and outstanding accuracy. A generic term for such a technique is "optical navigation." A hand held scanner and a mouse for a computer are among the devices that can use optical navigation, and examples are described in the incorporated patent documents.

Optical navigation techniques require that an illumination source (e.g. an Infra Red Light Emitting Diode, or IR LED) be used to create contrast in an image of the surface. To assist in the creation of shadows that reveal texture, the surface is generally illuminated from the side, and the result is often termed "grazing" illumination. The amount of reflected illumination reaching the photo sensitive detectors is termed "exposure." Exposure can be controlled in different ways. Among these are: controlling the open time of an electronic shutter while maintaining a constant level of incident illumination; controlling the intensity of a pulse of light issued while the electronic shutter is open (assuming there is one); and controlling the duration of a pulse of light occurring within the open time of an electronic shutter (again, assuming there is one).

Exposure varies considerably among different surfaces. Consider paper, which is perhaps the most frequently used surface. The type of fiber in a paper and the roughness and color of the paper, as well as information content related conditions like the presence of ink or fused toner, are all items that affect the amount of light incident upon the surface needed to create a certain level of exposure. Insufficient exposure fails to reveal contrast in the micro-texture ( the image sensor has a certain sensitivity that must be met), while over exposure "washes out" the image (and is either a saturation issue or a dynamic range limitation: the difference between bright and too bright). As an example of this phenomenon, consider the following table of different optimum exposure times at a constant level of incident illumination for different papers also having different image properties:

| | EXPOSURE TIMES (uSec) | |
|---|---|---|
| PAPER TYPE A | 10 | 2 |
| PAPER TYPE B | 20 | 4 |
| PAPER TYPE C | 30 | 8 |
| PAPER TYPE D | 40 | 10 |
| | LOW VARIANCE IMAGE | HIGH VARIANCE IMAGE |

It has been found that successful optical navigation over surfaces having differing properties requires that the illumination exposure be varied according to the conditions encountered. However, the task of adjusting the exposure during navigation as conditions vary is further complicated by the nature of the navigation process. It compares a reference image with successive images of micro-texture through a correlation process to determine the direction and amount of movement. After sufficient movement a new reference image is acquired. There is a high risk of compromising the comparisons if the level of incident illumination is allowed to vary at times other than when a reference image is being acquired.

It has also been found that simply adjusting the level of incident light to obtain some preselected median level of reflected light may not provide sufficient contrast for accurate navigation. A more sophisticated approach is required if optical navigation techniques are to more reliably operate over surfaces exhibiting widely varying surface conditions.

SUMMARY OF THE INVENTION

An acceptable exposure level for an optical navigation system is maintained by first establishing an initial operating level of exposure and subsequently adjusting it in proportion to changes in average illumination so long as image contrast remains acceptable. The initial operating level of exposure is obtained by first adjusting the exposure control parameter to until the average illumination is at a midrange value, and then inquiring if image contrast is within acceptable limits. If it is not, then the system hunts among different levels of exposure to find an adjusted trial level of exposure for which contrast is acceptable. This establishes the initial level of exposure, with which is associated an average level of illumination, which is then noted, and about which is presumed to exist a range of satisfactory operating levels for exposure. The system proceeds to navigate from the current reference frame using this level of exposure. When a new reference frame is established the average level of illumination and the image contrast are checked. If the illumination is within the range of presumed satisfactory operating levels for exposure and the image contrast is within acceptable limits, then no change is made to the parameter that adjusts exposure and navigation proceeds from the new reference frame. If average level of illumination is outside the presumed satisfactory range, but the image contrast is still acceptable, a proportional correction is made to the parameter controlling exposure, and navigation proceeds. In all other cases the contrast is unacceptable, and the -remedies are to variously re-enter the process that establishes an initial operating level for exposure.

DESCRIPTION OF A PREFERRED EMBODIMENT

Figure 1:
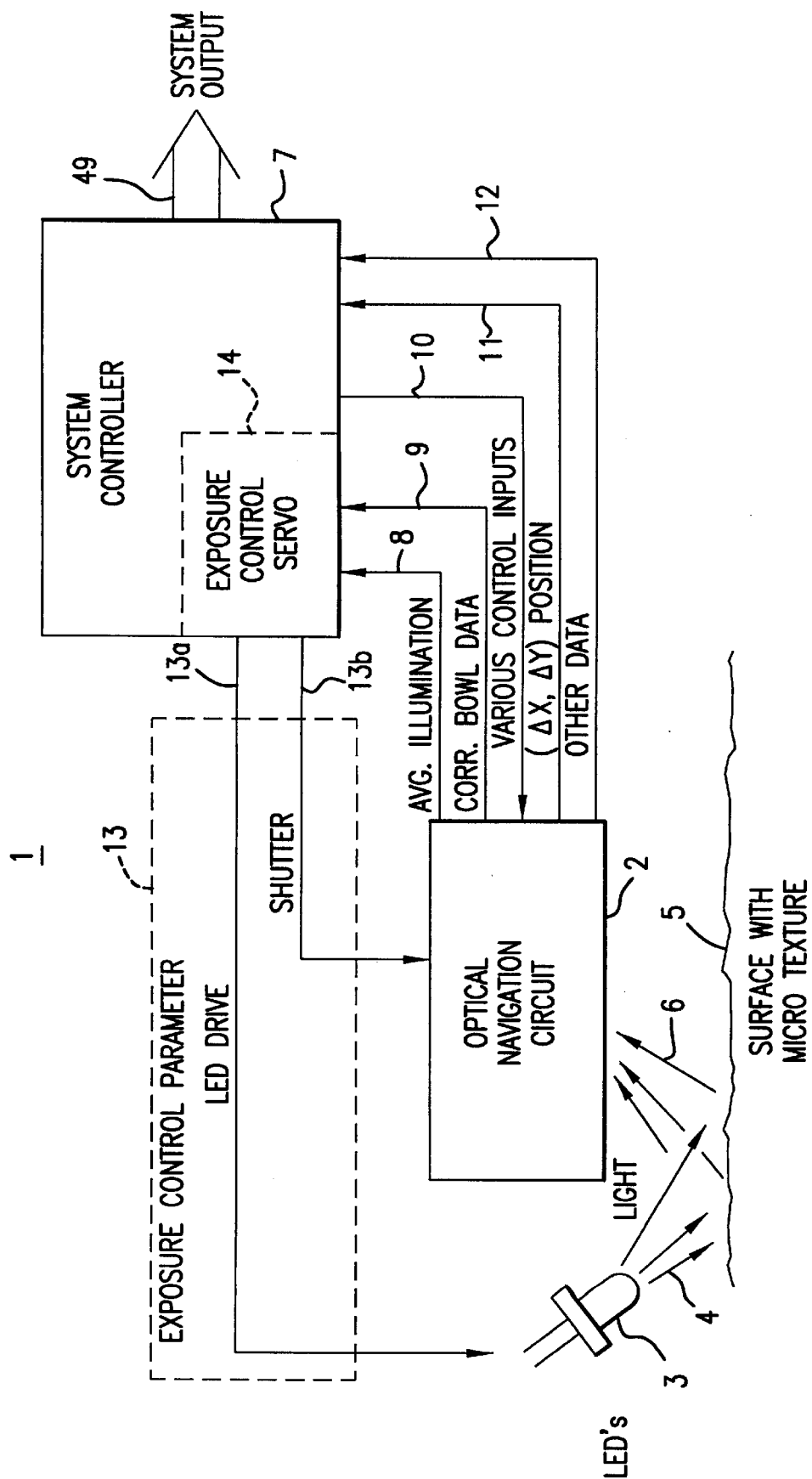
FIG. 1 is a simplified block diagram illustrating certain aspects of an environment for optical navigation in which it is beneficial to control exposure.

Refer now to FIG. 1, wherein is shown a simplified block diagram 1 of an optical navigation system. An optical navigation circuit 2, which may be as described or similar to those described in the incorporated material, is proximate a surface 5 whose micro-texture is illuminated by one or more LED's 3. Light 4 from the LED's 3 is reflected from surface 5, and some of that reflected light 6 enters an aperture (not shown) of the optical navigation circuit 2. The optical navigation circuit 2 registers changes in its physical location relative to the surface 5 by tracking the apparent motion of micro-texture produced patterns in an array of photo-sensitive devices (not shown) proximate the aperture. Correlation techniques between present and past frames of pixel images are used to do this, as explained in considerable detail in the incorporated documents. We term this process of tracking motion "navigation." It will be appreciated that the optical navigation circuit 2 is an IC (Integrated Circuit) of considerable size, and that it has an amount of self-contained processing power commensurate with the task. It is not by itself an entire system, however, and its outputs (8–12) are used by an outer layer of processing for some production of some result.

Accordingly, note that several outputs from the optical navigation circuit 2 are applied to a system controller 7 that does produce a system output 49 (e.g., a scanned image or a position). The outputs from the optical navigation circuit 2 include an average illumination value 8, correlation bowl data 9, incremental motion signals 11 for X and Y axes, and other data 12. In addition, there are other control inputs 10 that originate with the system controller 7, such as a reset signal, and other signals for various housekeeping functions.

One subsystem in the system controller 7 is of particular interest to us. It is an exposure control servo 14, whose output is an exposure control parameter 13, which may consist of two individual signals LED drive 13a and a shutter signal 13b. What we mean when we say that these two signals comprise a unitary exposure control parameter 13 is simply that these two signals do not vary independently while the exposure is under servo control. Think of the exposure control parameter 13 as a value that can vary from 0% to 100%, and as that variation happens there is a mapping that produces a pair of values, one for 13a and the other for 13b. Signals 13a and 13b are separate signals that may not have the same value, but they have a common source as to what their individual values ought to be. Nor is it necessary that both signals 13a and 13b be present. If the optical navigation circuit happened to use a constant light source, the LED drive signal 13a would instead be a power supply line and not be a part of a "control parameter." Likewise, it is possible (although perhaps not likely) that the optical navigation circuit does not have an electronic shutter, in which case signal 13b would be absent.

As a reminder, we said that exposure is the amount of reflected illumination reaching the photo sensitive detectors. Exposure can be controlled in different ways. Among these are: controlling the open time of an electronic shutter while maintaining a constant level of incident illumination; controlling the intensity of a pulse of light issued while the electronic shutter is open (assuming there is one); and controlling the duration of a pulse of light occurring within the open time of an electronic shutter (again, assuming there is one). The common source for signals 13 a and 13 b mentioned above is simply whatever rule is used to adjust exposure by one of the three methods mentioned above, or perhaps even by some other method.

Figure 2A:
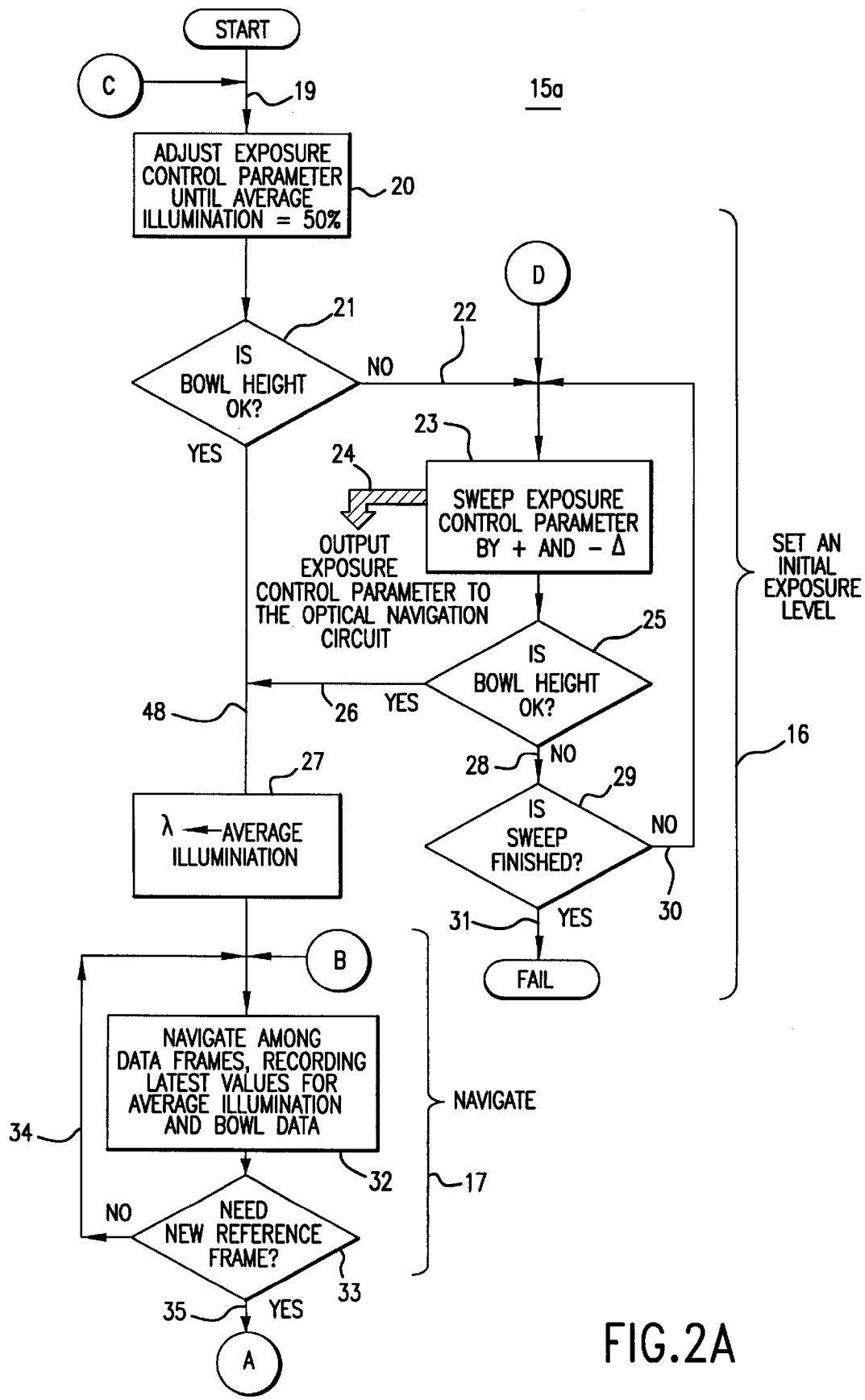
FIGS. 2A and 2B are a simplified flow chart of a method for controlling the exposure of an optical on system such as the one shown in FIG. 1.
Figure 2B:
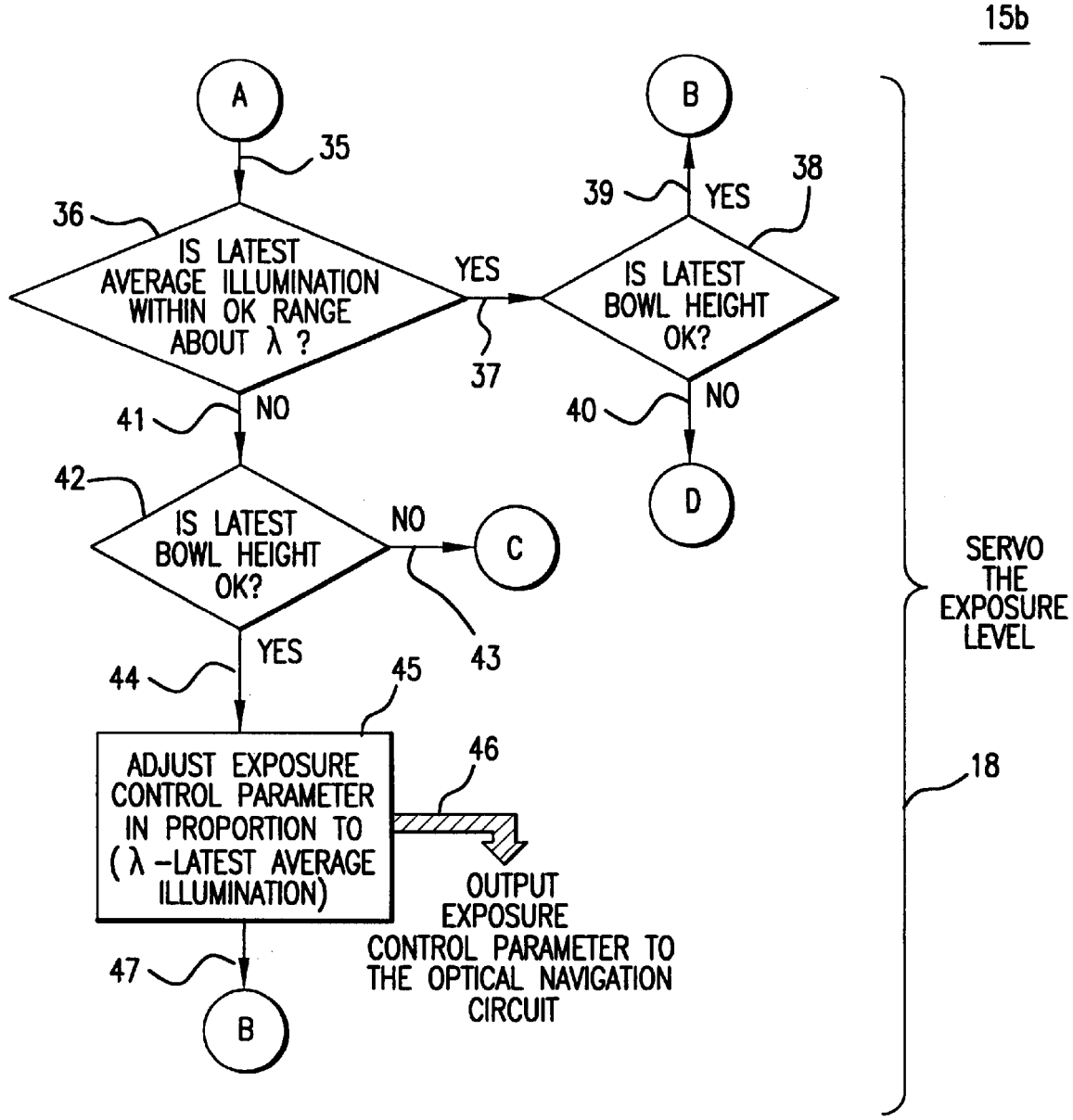

Refer now to FIGS. 2A and 2B, which are a flow chart 15a–b that describes the internal operation of the exposure control servo 14 of system controller 7. We begin at the START oval at the top of FIG. 2A. Path 19 leads to a step 20 which adjusts the exposure control parameter 13 until the average illumination 8 is at or close to 50% of its possible value. A condition of no reflected light 6 produces a 0% value of average illumination, while the light reflected from some maximally reflective surface is used to define what is to correspond to 100%. The particulars of how much average illumination corresponds to what percentage is a design issue related to internal operation of the optical navigation circuit 2, and may be considered here as simply a built-in property of that circuit. Average illumination 8 may be derived from summing the amplitudes of all the photo-detector outputs for the latest frame.

Once the average illumination is initially set by step 20, qualifier 21 asks if the "bowl height is okay". Once again we pause briefly to digress. Recall that we said that navigation involves tracking apparent movement of a pixel pattern. This is realized by comparing a data frame to a reference frame. The comparison is made by shifting the contents of one frame relative to the other by one pixel in some direction and asking if the pixel values in the various locations are the same (or, is the sum of all their respective differences zero, or so). The comparison "in some direction" is performed for a pixel displacement in all directions: one up, one down, one left, one right, one up and one left, one up and one right, one down and one left, and, one down and one right. That is a total of eight comparisons. But we mustn't forget that there might have been no movement, so we also need result for no shifting. That makes nine comparison values that correspond in principle to what we have termed correlation values. The one that is the lowest represents the relative motion we are tracking. To be more robust in this process, we could go also to the next nearest pixel positions, which would raise the number of correlation values to twenty-five. The correlation process is explained in considerable detail in the incorporated documents. The "bowl" is simply the three dimensional plot of the correlation amplitudes versus the shifted position they represent. The significance of the bowl, besides indicating movement or the lack thereof is that its shape gives rise to confidence that the navigation process is working as it is intended to. For example, if the bowl is "flat" we can presume that there is insufficient contrast amongst the pixels to navigate upon. That is a serious situation that is to be avoided during navigation. Lack of excursions in the bowl may be brought on by changes in the surface as navigation proceeds, and might be correctable by changes in exposure. Indeed, that is the underlying purpose of the flowchart 15a–b of FIGS. 2A–B, whose explanation we now resume.

So, the qualifier at step 21 determines if the bowl has sufficient excursion, which is essentially determined by image contrast. Suppose the bowl does not have the needed height. Then path 22 leads to step 23 whose function is to vary, or sweep, the exposure control parameter through its range to find a level of exposure that has sufficient image contrast to navigate upon. To this end, step 23 changes the exposure control parameter 13 by some amount ($\Delta$), outputs that value (24) to the optical navigation circuit 2, and then step 25 checks to see if the bowl is usable. If the answer is "NO," then path 28 leads to step 29 where it determined if the sweep run its course. If the answer at step 29 is "NO," then there are yet different values of exposure to try, and path 30 returns to step 23 to try the next one. Otherwise, if the sweep is finished, there is no hope of navigating normally, and path 31 leads to some process that deals with such failure. If adjusting exposure is effective, then after some instance of step 23 the qualifier at step 25 will exit with a "YES" on path 26, which leads to path 48.

Path 48 is also the "YES" exit from qualifier 21, which if it happens, represents the case where the initial setting of the exposure control parameter 13 at step 20 did indeed produce a useable bowl. Path 48 leads to step 27, where the current value of average illumination is stored for future reference. We call stored value $\lambda$. At this point we have completed the sub-process 16 called SET AN INITIAL EXPOSURE LEVEL.

The next sub-process 17 is called NAVIGATE. It is here that step 32 represents the tracking of movement, accompanied by the storing and outputting of the latest values of average illumination 9 and the collection latest correlation values 9. After each data frame an inquiry is made with step 33 to determine if the navigation process is getting close to "falling off the edge of the reference frame." If not, then navigation can continue (path 34), and the exposure control parameter 13 is left unchanged. If it is, however, then a new reference frame is needed, and path 35 to point A (see FIG. 2B) leads to the sub-process 18 SERVO THE EXPOSURE LEVEL, which will allow for the adjustment of the exposure level, if needed.

Refer now to FIG. 2B, where path 35 resumes from point A and leads to a qualifier step 36, where it is asked if the latest average illumination (stored back in step 32) remains within a selected range of $\lambda$. The range could be from $\lambda/2$ to $2\lambda$. If it is, then continued navigation with the same general level of exposure may be possible, provided the bowl is still okay. To this end, path 40 leads to qualifier step 42, where the latest bowl height is checked. If it is indeed okay then step 45 applies a fine correction to the exposure level parameter 13 by an amount that is proportional to the change away from $\lambda$ in latest average illumination. After this is done the adjusted value for the exposure control parameter is output (46) to the optical navigation circuit 2, and path 47 transitions (point B) to step 32 in the NAVIGATE sub-process 17.

Note that if the bowl is bad at step 42, then path 43 transitions (point C) to step 20 in FIG. 2A. This represents the case where both the level of illumination has changed significantly and the bowl is not useable. It is a total start over situation.

Now, to return to step 36, if the answer there was "YES" then the exposure level is essentially unchanged, and path 37 leads to qualifier 38, where the bowl is checked again. If it is good, then path 39 leads (via point B) back to step 32 in the NAVIGATE sub-process 17 of FIG. 2A. If, on the other hand, the bowl has gone bad the exposure level needs to be reset. Path 40 leads (via point D) to step 23 in the SET AN INITIAL EXPOSURE LEVEL sub-process 16 of FIG. 2A. This is similar to the total start over situation (point C), except that it is known that the average illumination level is probably a workable value, so that step 20 in the sub-process 16 can be skipped.

We claim:

1. A method of adjusting an exposure control parameter in an optical navigation system in relative motion with respect to a work surface, the method comprising the steps of:
    (a) initially varying the setting of the exposure control parameter until average illumination is approximately 50% of its maximum possible value;
    (b) subsequent to step (a), retaining, if correlation data associated with navigation are satisfactory, the current exposure control parameter setting, otherwise further varying the exposure control parameter setting to obtain satisfactory correlation data;
    (c) subsequent to step (b), storing the average level of illumination produced by the navigation system when operating with the exposure control parameter setting produced by step (b);
    (d) navigating with the exposure control parameter setting produced by step (b) until a selected amount of relative motion has occurred between the optical navigation system and the work surface, the navigation including storing latest values of average illumination and latest values of the correlation data; and
    (e) subsequent to step (d), adjusting the setting of the exposure control parameter, the adjusting comprising:
        (e1) determining if the most recently stored latest value of average illumination is within a selected range about of the average illumination level stored in step (c);
        (e2) if step (e1) is in the affirmative: returning to navigation step (d) if the most recently stored latest values of the correlation data are satisfactory, and otherwise returning to retaining step (b); and
        (e3) if step (e1) is in the negative: returning to step (a) if the most recently stored latest values of the correlation data are unsatisfactory, and otherwise adjusting the exposure control parameter by an amount proportional to the value of the average illumination stored in step (c) diminished by the most recently stored latest value of average illumination, and then returning to navigating step (d).

2. A method as in claim 1 wherein the setting of the exposure control parameter determines a length of time that an electronic shutter is open.

3. A method as in claim 1 wherein the setting of the exposure control parameter determines the intensity of a pulse of light.

4. A method as in claim 1 wherein the setting of the exposure control parameter determines the duration of a pulse of light.

5. A method as in claim 1 wherein the navigating step (d) supplies position data used to track the motion of a hand held device controlling the location on a computer monitor of a screen pointer.

6. A method as in claim 1 wherein the navigating step (d) supplies position data used to track the motion of a hand held scanner.

* * * * *